United States Patent [19]

Han et al.

[11] 4,241,602
[45] Dec. 30, 1980

[54] RHEOMETER

[75] Inventors: Chang D. Han, Nutley, N.J.; Vance Morrow, Tulsa, Okla.

[73] Assignee: Seismograph Service Corporation, Tulsa, Okla.

[21] Appl. No.: 31,900

[22] Filed: Apr. 20, 1979

[51] Int. Cl.³ ............................................. G01N 11/04
[52] U.S. Cl. ........................................................ 73/56
[58] Field of Search .................... 73/56, 55, 54, 15.4

[56] References Cited

U.S. PATENT DOCUMENTS

| | | | |
|---|---|---|---|
| 3,048,030 | 8/1962 | De Haven | 73/56 |
| 3,952,577 | 4/1976 | Hayes et al. | 73/55 |

FOREIGN PATENT DOCUMENTS

442808  1/1968  Switzerland ................... 73/56

*Primary Examiner*—Gerald Goldberg
*Assistant Examiner*—Joseph W. Roskos
*Attorney, Agent, or Firm*—Mason, Kolehmainen, Rathburn & Wyss

[57] ABSTRACT

A high precision continuous flow rheometer utilizes an elongated restriction such as a slit or capillary tube that is supplied with fluid from a microprocessor controlled metering pump at various flow rates. An inlet chamber having a longitudinal axis that is skewed with respect to the longitudinal axis of the restriction is used to convey fluid from the metering pump to the restriction. Three pressure transducers are disposed along the slit or capillary tube and supply signals to the microprocessor from which the viscosity and elasticity, or first normal stress difference, of the fluid may be continuously calculated at various flow rates.

20 Claims, 16 Drawing Figures

RHEOMETER

BACKGROUND OF THE INVENTION

1. Field of the Invention

This invention relates generally to rheometers, and more particularly to a computer controlled rheometer that provides analysis of the viscosity and elasticity of a product to permit optimum control of the manufacture or utilization of the product.

2. Description of the Prior Art

Rheometers, including rheometers that employ a restriction, such as a slit or a capillary are known. Such prior art rheometers fall into two general categories. The first category includes laboratory type rheometers wherein a small sample of a fluid to be analyzed is manually applied to the rheometer and the properties of the fluid are determined from manual calculations based on manually read pressure readings. The second category includes industrial type rheometers which generally measure only a single parameter of the fluid, such as viscosity, and are not particularly accurate. Typical prior art rheometers are disclosed in U.S. Pat. Nos. 2,834,200; 3,138,950; 3,841,147 and 4,027,526.

SUMMARY OF THE INVENTION

Accordingly, it is an object of the present invention to provide an improved rheometer that overcomes many of the disadvantages of the prior art rheometers.

It is another object of the present invention to provide an automatic rheometer that continuously measures both fluid viscosity and fluid elasticity with a high degree of accuracy.

It is another object of the present invention to provide an improved restriction type rheometer utilizing a slit or capillary for measuring both fluid viscosity and fluid elasticity over a wide range of shear rates.

It is yet another object of the present invention to provide a computer controlled rheometer that analyzes the parameters of a fluid rapidly enough to provide on-line control of the fluid manufacturing or fluid utilization operations, particularly in the polymer manufacturing and polymer fabricating fields.

It is yet another object of the present invention to provide a restriction type rheometer having an improved design inlet chamber disposed between the restriction and the fluid metering pump.

It is yet another object of the present invention to provide a rheometer that has a computer controlled metering pump.

In accordance with a preferred embodiment of the invention, there is provided an elongated restriction such as a slit or capillary die that is fed by a metering pump such as a positive displacement gear pump. The gear pump is driven by a computer controlled electric motor and feeds the fluid into the die at various pre-programmed flow rates. Three pressure transducers are disposed along the slit or capillary in a region of fully developed flow, and electrical signals proportional to the pressure sensed by the three transducers are applied to the computer which utilizes the pressure information to determine the viscosity and elasticity of the fluid being tested. The computer is also programmed to adjust the speed of the electric motor periodically and at a predetermined rate so that the viscosity and elasticity may be determined at various flow rates. An improved inlet chamber having a longitudinal axis that is skewed with respect to the longitudinal axis of the slit or capillary provides simplified construction and an excellent interface between the metering pump and the restriction.

BRIEF DESCRIPTION OF THE DRAWING

These and other objects and advantages of the present invention will become readily apparent from a consideration of the following detailed description and attached drawing wherein.

DETAILED DESCRIPTION OF THE PREFERRED EMBODIMENT

I. General

Figure 1:
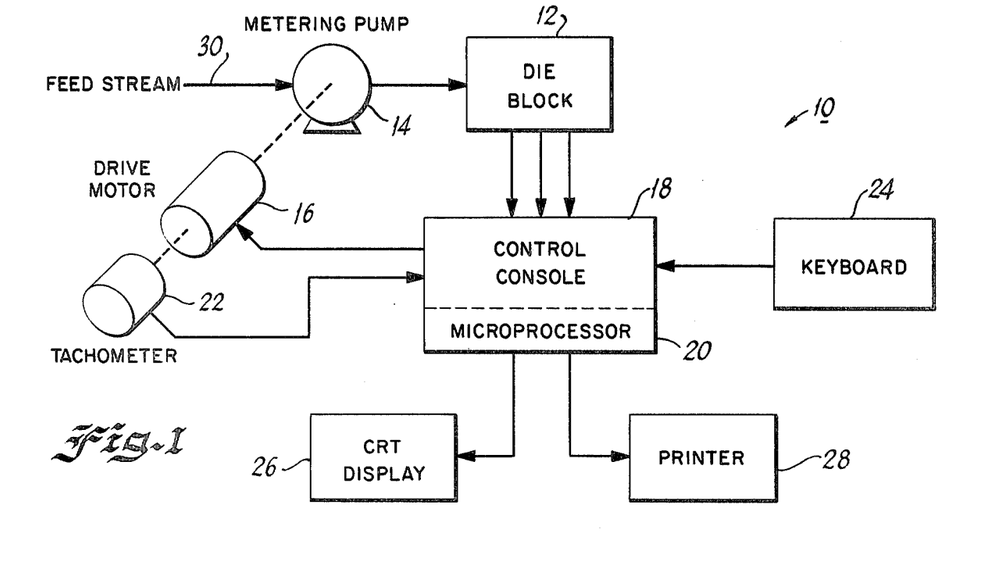
FIG. 1 is a functional block diagram of the rheometer according to the invention.

Referring now to the drawing, with particular attention to FIG. 1, there is shown a block diagram of the rheometer according to the invention, generally designated by the reference numeral 10. The rheometer 10 contains a die block 12 which contains a restriction, such as, for example, a slit or capillary die through which the fluid being analyzed is forced by a metering pump 14. The metering pump 14 is driven by a drive motor 16 under the control of a control console 18 that, in the present embodiment, contains a microprocessor 20. A tachometer 22 provides a signal representative of the speed of the motor 16 to the control console. A keyboard 24 is used to input data into the control console 18 and a cathode ray tube display 26 and a printer 28 are used to display various data about the fluid being analyzed.

In operation, the metering pump 14 receives the fluid to be analyzed from a feed stream 30 and applies it to the die block 12. The metering pump 14 is a positive displacement gear pump, and thus, the flow rate of the fluid applied to the die block 12 is determined by the speed at which the metering pump 14 is driven by the drive motor 16. The feed stream 30 is designed to have sufficient capacity to supply the metering pump at all pump speeds to assure that the speed of the drive motor 16 provides an accurate indication of the flow rate of the fluid being applied to the die block 12. The die block 12 contains a long, narrow restriction, such as a slit or capillary die. If the fluid being analyzed is an elastic fluid, such as a non-Newtonian fluid, a certain amount of elastic energy will be stored in the fluid during the flow. This stored energy can be measured by pressure transducers positioned along the length of the slit or capillary die, and from these pressure measurements, the exit pressure and the viscosity and elasticity or first normal stress difference of the fluid may be calculated. In the present invention, the calculations are made by the microprocessor 20, and the results of the calculations are displayed on either the cathode ray tube display 26 or the printer 28, or both.

The keyboard 24 is used to enter various parameters and test conditions into the control console 18. Typical parameters that may be entered by means of the keyboard 24 include, for example, the geometry of the slit or capillary die, such as the height and width of the slit or diameter of the capillary, the size or displacement of the metering pump 14, the temperature of the die and the desired speed and direction of rotation of the metering pump 14. Several pump speeds may be entered by means of the keyboard 24 along with the length of time that the pump is to run at each of the selected speeds as well as the rate at which the transition between speeds is to occur. This makes it possible to program the pump to supply fluid to the die block 12 automatically and at various flow rates, and permits measurements of elasticity and viscosity to be taken automatically at the preprogrammed flow rates. This feature is particularly important when a fluid, such as a molten polymer, whose viscosity and elasticity vary as a function of shear rate is being analyzed.

Figure 2:
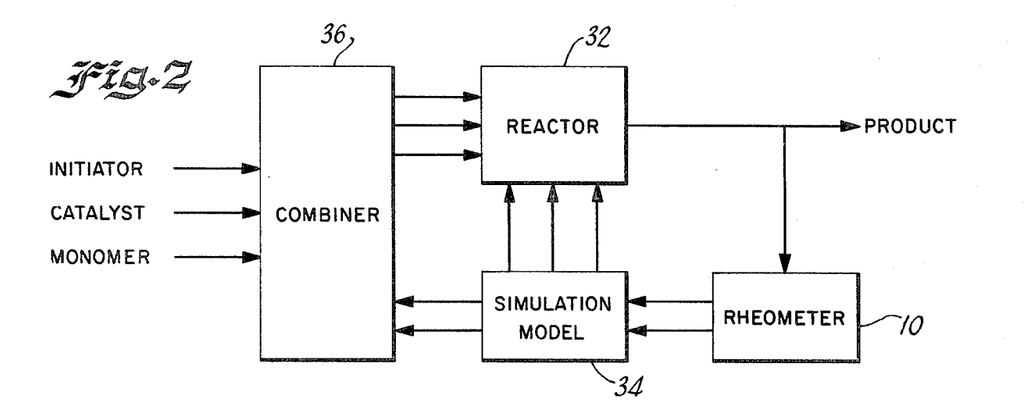
FIG. 2 is a block diagram showing the rheometer according to the invention used to provide on-line control of a polymerization reactor.

While the rheometer 10 illustrated in FIG. 1 may be used to measure the viscosity and elasticity of any fluid, including gases and food products, such as, for example, mayonnaise and molten process cheese, the rheometer according to the invention is particularly useful for providing on-line control of polymer manufacturing and fabrication processes. For example, the rheometer 10 can be connected to the output of a polymerization reactor 32 (FIG. 2) in order to monitor the quality of the polymer being produced by the reactor 32. In this connection, the rheometer according to the invention is particularly useful since an elasticity or first normal stress difference measurement provides a much more sensitive indication of quality than the viscosity measurement provided by the prior art rheometers. Also, as a result of the speed at which the measurements may be taken with the present rheometer, the polymer produced by the reactor 32 may be continuously monitored by the rheometer 10, and continuous readings of the viscosity and elasticity of the polymer provided. These readings may then be applied to a simulation model 34, which could be used to control the operation of the reactor 32 as well as a combiner 36 in order to vary the relative proportions of the initiator, catalyst and monomer applied to the reactor 32. Thus, the rheometer provides an on-line closed loop system that tightly controls the parameters of the polymer produced by the reactor 32 in order to provide a polymer of more consistent quality than could be heretofore achieved.

Figure 3:
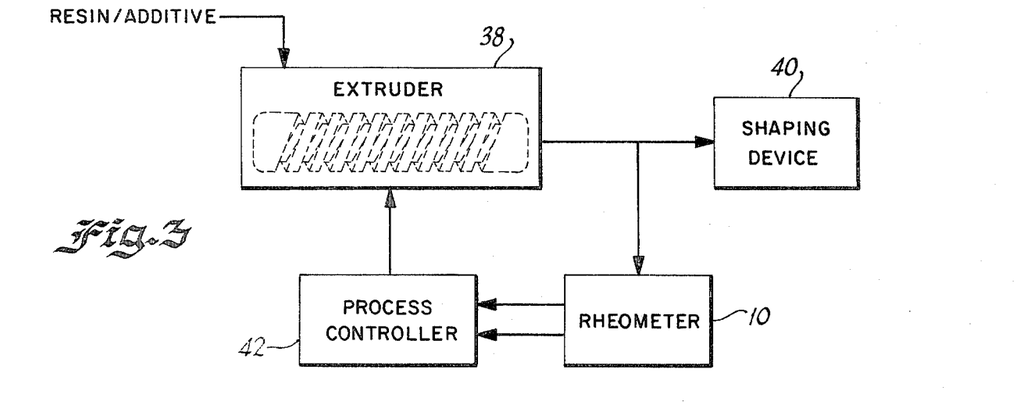
FIG. 3 is a block diagram showing the rheometer according to the invention used to provide on-line control of a polymer fabrication operation.

The rheometer 10 may also be used to provide closed loop on-line control of the fabrication of the polymer into a final product. In such a fabrication operation, the rheometer 10 could be used to sample the output of an extruder 38 (FIG. 3) in order to determine whether the properties of the physical polymer are such that the polymer will be properly shaped by a shaping device 40. If the physical properties of the polymer vary, any change will become readily apparent from the polymer viscosity and elasticity readings, particularly the latter. Because the readings of viscosity and elasticity made by the rheometer are so sensitive, they may be used to control a process controller 42 in order to adjust the operation of the extruder or the proportion of resin and additive applied to the extruder. In this manner, the physical properties of the polymer are optimized, and more nearly optimum performance of the shaping device 40 is achieved. As a result of the more precise control of the fabrication operation, the number of rejects produced is substantially reduced.

Figure 4:
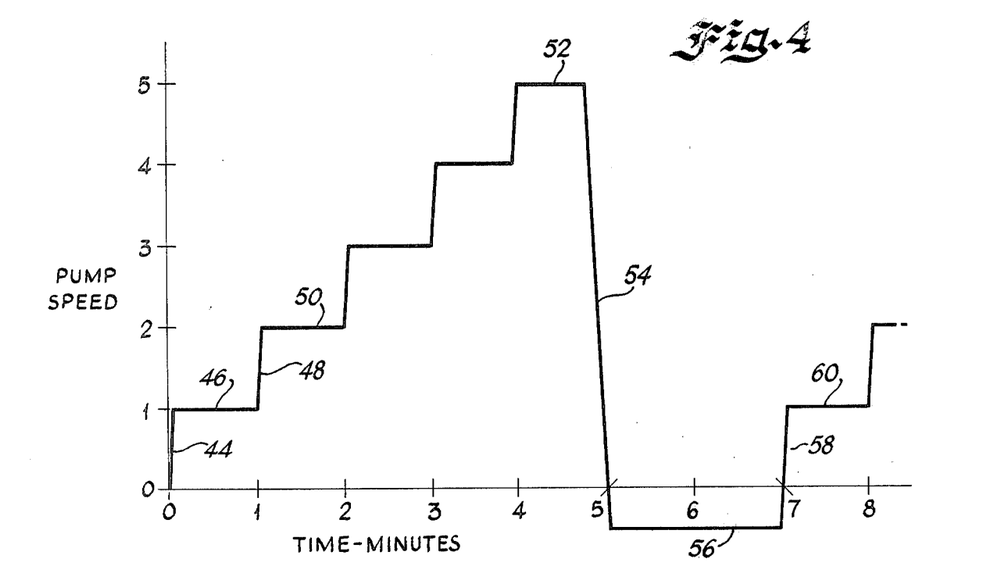
FIG. 4 is a graph illustrating a typical operating cycle of the rheometer according to the invention.

The physical properties of most polymers, including viscosity and elasticity, vary as a function of shear rate which is a function of flow rate or pump speed. Thus, it is desirable to measure the parameters of the polymer at various shear rates or pump speeds. As previously discussed, the rheometer according to the present invention is particularly suited for making measurements over a wide range of shear rates. A typical program for measuring the viscosity or elasticity of a fluid over a wide range of shear rates is illustrated in FIG. 4. In the program illustrated in FIG. 4, the pump speed is increased from a standstill to a first predetermined pump speed. The increase in the speed of the pump is illustrated by the segment 44 of the graph of FIG. 4. The speed of the pump is then maintained constant at the first predetermined speed as illustrated by the segment 46. In the illustration of FIG. 4, the speed of the pump is maintained at the first predetermined time speed for a period of approximately one minute, however, this time period can be adjusted in accordance with the characteristics of the fluid being analyzed. In general, however, the time is selected to be of sufficient duration to allow the fluid to reach a steady-state flow through the rheometer and to permit several measurements to be taken after steady-state flow has been achieved. The time required for a steady-state flow, as characterized by a constant pressure reading may range from the order of approximately 30 seconds to approximately 240 seconds for a typical polymer. Thus, it is apparent that both the time duration between steps as well as the time delay before a measurement can be taken is extremely variable. Consequently, the portion of the time interval between pump speed changes during which measurements may be taken ranges from the last 10% of the interval to the last 90% of the interval, depending on the absolute value of the time interval and the polymer being analyzed.

After a sufficient number of measurements have been taken, the speed of the pump is increased to a second predetermined pump speed as illustrated by the segment 48, and maintained at the second speed for a predetermined time as illustrated by the segment 50. Measurements are again taken after the fluid has reached a steady-state flow and the speed of the pump is again advanced several more times and pressure measurements are taken at each of the various pump speeds. The pump speeds may be individually programmed and may be either uniformly, as shown in FIG. 4, or non-uniformly spaced.

Since most polymers being tested exhibit at least some degree of elasticity, if the speed of the pump were changed instantaneously or very rapidly, the accelerations caused by such a rapid change in pump speed would cause pressure transients that would take a considerable amount of time to dissipate. Since such transients would slow down the measuring process, the speed of the pump is increased at a predetermined, controlled rate to minimize such transients and permit more rapid measurements. The rate at which the pump speed is changed depends on the characteristics of the fluid being measured, and is generally determined empirically. Once the rate for a particular polymer has been determined, it can be programmed into the microprocessor 20 so that the optimum transition between pump speeds is automatically achieved.

After pressure measurements have been taken at the highest programmed pump speed, as illustrated by the segment 52, it is desirable to reduce the pump speed to the first predetermined level and repeat the measurements several times to improve overall system accuracy. However, after the pump has been running at the maximum programmed speed, a great deal of pressure is built up within the die block. Since the slit or capillary has relatively small dimensions, a considerable amount of time is required for the built-up pressure to dissipate. The amount of time required depends on the geometry of the slit or capillary and on the relaxation time of the polymer or other fluid being analyzed. Therefore, if the pump speed were simply reduced to the first predetermined pump speed and pressure measurements were taken, the pressure readings taken would be erroneously high. Accordingly, in accordance with another important aspect of the invention, a relaxation cycle is built into the pump control sequence in order to permit the stored energy to be dissipated more quickly. The dissipation of the energy is accomplished by either stopping the pump for a predetermined length of time sufficiently long to permit the energy to dissipate, or by running the pump in reverse for a predetermined length of time to release the pressure. The latter approach is particularly useful for fluids that contain a large amount of stored energy since reversing the pump direction substantially reduces the amount of time required to reduce the pressure to zero.

The relaxation cycle is illustrated by segments 54 and 56 (FIG. 4) which show the speed of the pump being reduced along segment 54 until the pump is driven in reverse as illustrated by segment 56. The pump is then operated in the reverse direction for a predetermined length of time sufficient to eliminate the built-up pressure from the die block 12. After the excess pressure has been eliminated, the speed of the pump is again gradually increased along segment 58 to the first predetermined speed illustrated by segment 60, and the cycle is repeated.

The use of the control console 18 and the microprocessor 20 makes it relatively easy to program any desired pump speed sequence by simply entering into the control consoles each desired pump speed and the time interval that each speed is to be maintained. The microprocessor then generates a timing signal proportional to the selected speed which is compared with the frequency of the signal obtained from the tachometer 22. The power applied to the drive motor 16 is adjusted until the frequency of the tachometer generated signal is equal to the frequency of the microprocessor generated signal. When the preselected time interval has elapsed, the frequency of the microprocessor generated signal is simply increased, as is the power applied to the drive motor 16 until the frequency of the tachometer signal is increased to the new frequency of the microprocessor generated signal.

To achieve an increase in pump speed at a controlled rate, the frequency of the microprocessor generated signal is simply increased in a controlled fashion and the speed of the drive motor increases at a corresponding rate. The rate of increase of the frequency of the microprocessor generated signal may be entered via the keyboard 24, or may be stored in an internal memory within the control console. The last mentioned memory may also contain other information such as calibration information of the pressure transducers, and a maximum safe pressure limit. The maximum safe pressure limit serves as a safety feature in the event that a pump speed that would result in excessive pressure is inadvertently selected. The microprocessor is programmed to select a reduced pump speed that would produce the maximum pressure that could be tolerated by the system if a speed that would produce excessive pressure is selected and to record data taken at the reduced pump speed. Thus, meaningful information is obtained even when the operator makes an error.

II. Die Block Description

Figures 5, 6:
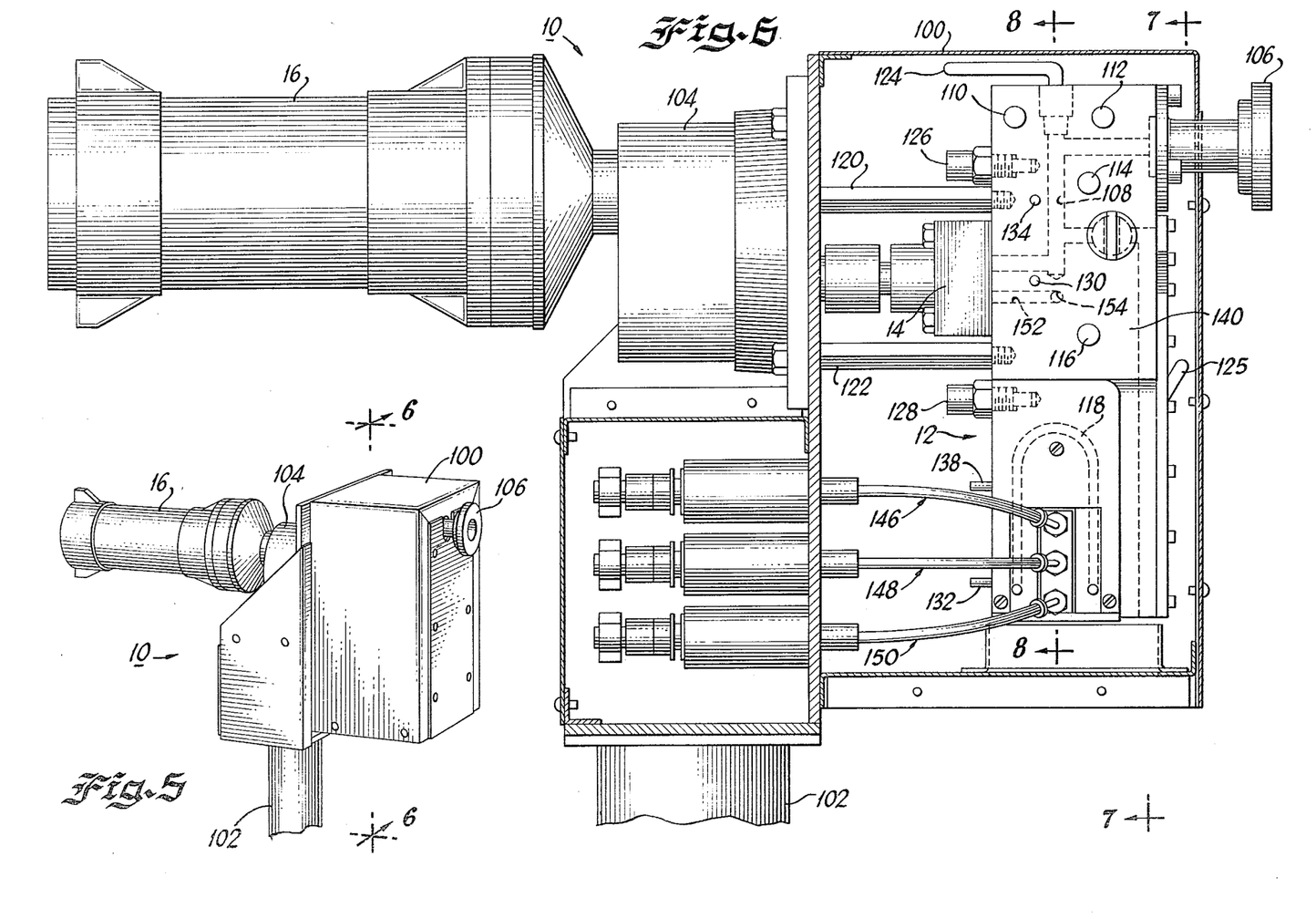
FIG. 5 is a perspective view of a portion of the rheometer according to the invention showing the die block housing and the driving motor for the metering pump.
FIG. 6 is a side cross-sectional view taken along line 6—6 of FIG. 5 showing the die block of the rheometer according to the invention.
Figures 9, 12, 13:
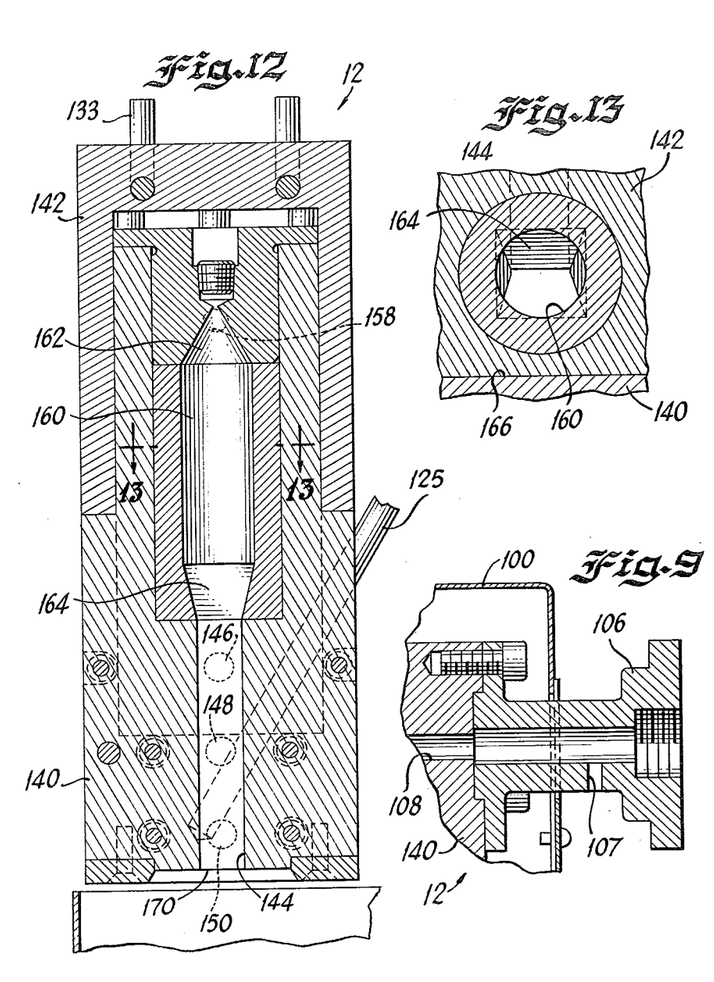
FIG. 9 is a sectional view taken along line 9—9 of FIG. 7.
FIG. 12 is a sectional view of the die block taken along line 12—12 of FIG. 8.
FIG. 13 is a sectional view of the die block taken along line 13—13 of FIG. 12.

The die block 12 is contained in a housing 100 (FIGS. 5 and 6) which is supported by a support member 102 and supports the drive motor 16 by means of a gear box 104 (not shown in FIG. 1). The gear box 104 is a speed reduction unit that reduces the shaft speed of the motor 16 to a lower speed suitable for driving the pump 14, which in the present embodiment is a Zenith melt pump; however, any suitable positive displacement pump may be used. The die block 12 contains an inlet fitting 106 and a passageway 108 for conducting the fluid from the inlet fitting 106 to the metering pump 14. A passageway 107 (FIG. 9) is provided within the inlet fitting 106 to allow excess material that cannot be handled by the metering pump 14 (particularly at low pump speeds) to escape.

Figure 7:
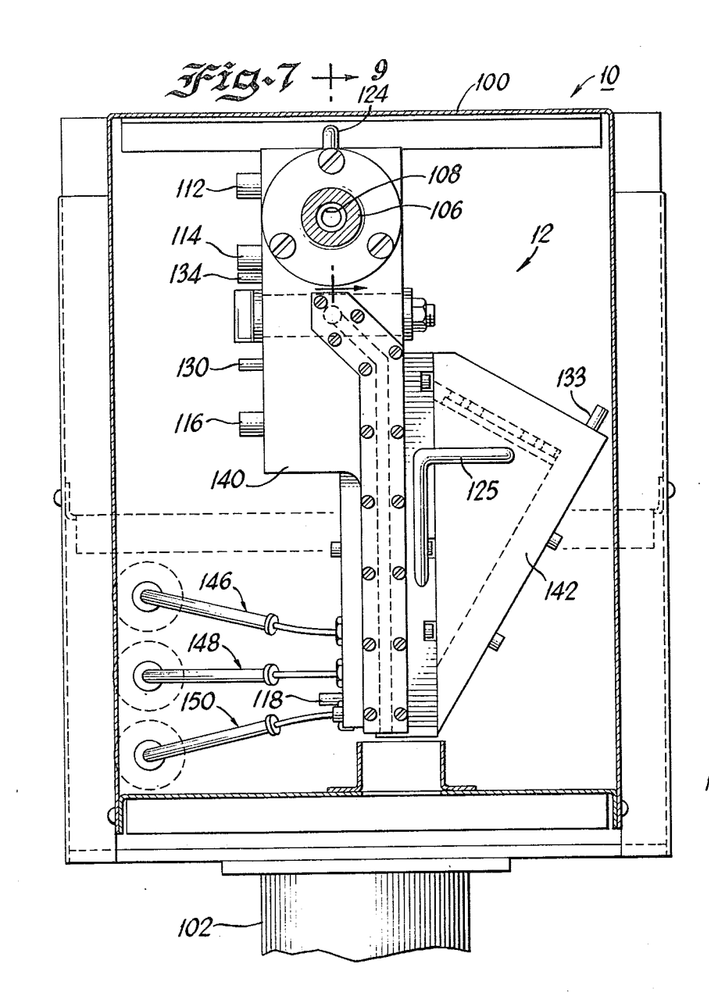
FIG. 7 is a sectional view taken along line 7—7 of FIG. 6 showing an end view of the die block.

A plurality of heaters 110, 112, 114, 116 and 118 maintain the die block 12 at an elevated temperature in order to maintain the polymer being analyzed in a molten state. In addition, a pair of support members 120 and 122 and a similar pair of support members 121 and 123 (FIG. 8) serve to conduct heat away from the die block 12 to the housing 100. The use of the heaters 110, 112, 114, 116 and 118 in conjunction with the heat conducting supporting rods 120 through 123 provides accurate control of the temperature of the fluid being analyzed over a wide range of temperatures of the fluid applied to the inlet coupling 106. If the temperature of the fluid applied to the inlet coupling 106 is excessive, the excess heat is conducted to the housing 100 by means of the conducting rods 120 and 122. If the temperature is too low, the heaters 110, 112, 114, 116 and 118 are energized to raise the temperature to the desired level. A thermometer 124 in communication with the passageway 108 provides an indication of the temperature of the fluid in the upper portion of the die block 12, and a similar thermometer 125 (FIGS. 7 and 10) provides an indication of the temperature of the fluid in the lower portion of the die block 12. An under-temperature protection switch 126 and an over-temperature protection switch 128 protect the system in the event of a failure in the temperature control system. Both a high temperature and a low temperature protection switch are necessary since excessively high temperatures can overheat the system, possibly resulting in a fire, while excessively low temperatures would allow the polymer being analyzed to solidify. If the polymer were to solidify, the various passageways in the die block could clog and the gear pump could be damaged.

Figures 8, 10, 11:
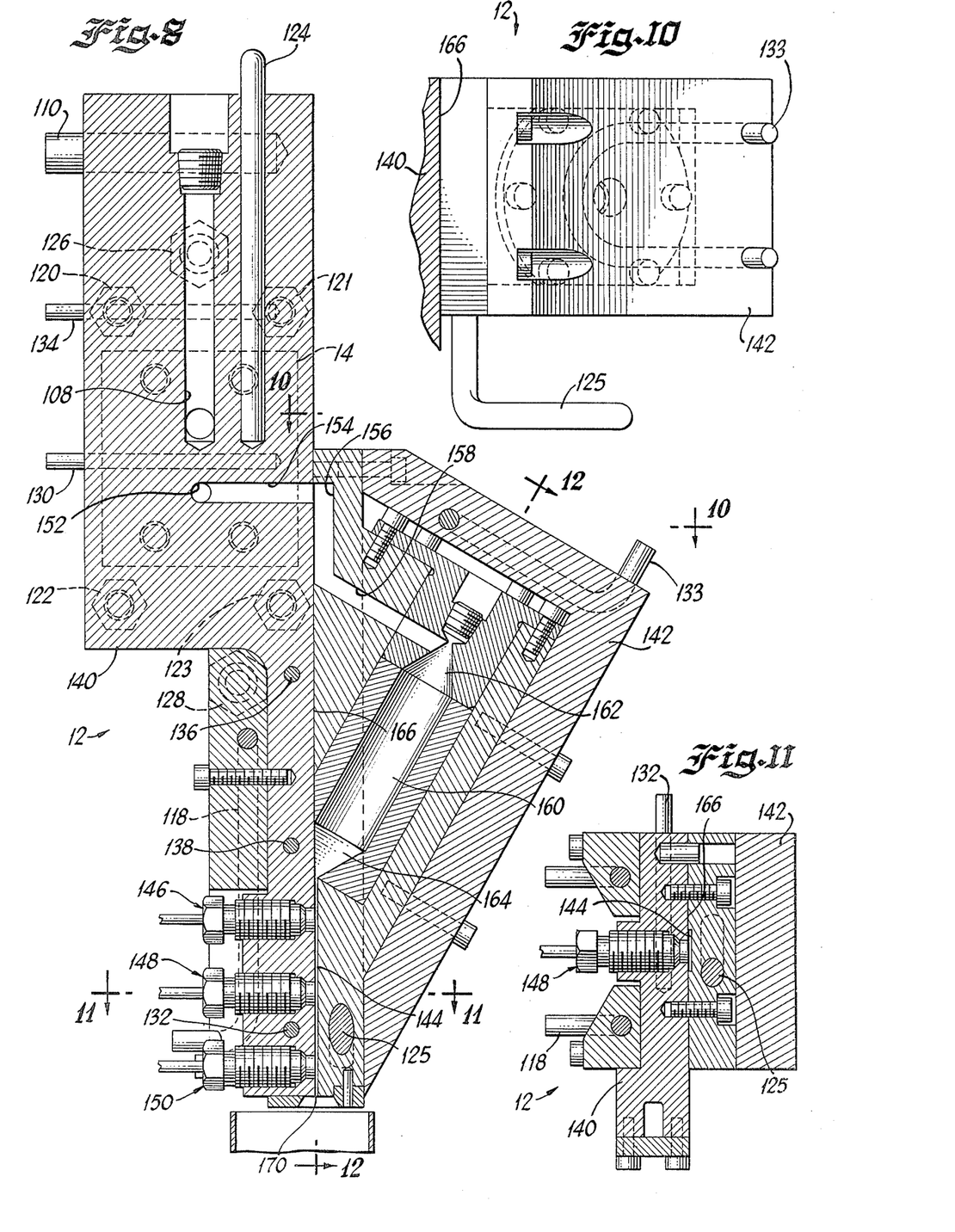
FIG. 8 is a sectional view taken along line 8—8 of FIG. 6 showing the inner passages of the die block.
FIG. 10 is a sectional view of the die block taken along line 10—10 of FIG. 8.
FIG. 11 is a sectional view of the die block taken along line 11—11 of FIG. 8.

Except for the function provided by the over-temperature and under-temperature protection switches 128 and 126, respectively, the heaters are controlled by the control console 18 and a pair of temperature sensing elements such as thermistors 130 (FIG. 6) and 132 (FIG. 8). The thermistor 130, or similar temperature sensing element, is electrically coupled to the control console 18 and serves to control the temperature of the upper portion of the die block 12 by controlling the energization of the electric heaters 110, 112, 114 and 116. Similarly, the thermistor 132, or similar temperature sensing element, is coupled to the control console 18 and serves to control the temperature of the lower portion of the die block 12. An optional heater, such as a heater 133, may be located in another portion of the die block 12 and also controlled by the thermistor 132 to provide even more precise control of the temperature. Thus, the temperature of the die block 12 is accurately controlled by the microprocessor 20, and any temperature can be selected either by entering the desired temperature into the microprocessor 20 by means of the keyboard 24, or by permanently programming the microprocessor 20 utilizing a read-only memory or the like. Also, as a result of the use of separate temperature sensing thermistors in the upper and lower portions of the die block 12, the upper and lower portions may be maintained at different temperatures. In addition, provision is made for other temperature sensing elements 134, 136 and 138 should even more precise temperature control be desired. Alternatively, the outputs of the temperature sensing thermistors 130 and 134, and 132, 136 and 138 may be combined to better control the average temperatures of the upper and lower portions of the die block 12.

In accordance with another important aspect of the invention, the die block 12 includes a support block 140 and a removable capillary block 142. The support block 140 and the capillary block 142 cooperate to form a slit 144 at the lower end thereof, and three pressure transducers 146, 148 and 150 are mounted near the lower end of the support block 140 adjacent to the slit 144. Although the support block 140 and the capillary block 142 cooperate to form a slit in the illustrated embodiment, it should be noted that the support block 140 and capillary block 142 could be shaped so that another type of restriction, such as a capillary tube, rather than a slit is formed. The pressure transducers 146, 148 and 150 serve to measure the pressure gradient along the length of the slit 144 when fluid is pumped through the slit 144 by the metering pump 14. More than three transducers may be used, if desired.

The fluid from the metering pump 14 is applied to the slit 144 through a passageway 152 in communication with the pump 14 and a passageway 154 that is disposed at a right angle to the passageway 152. The passageway 154 is in communication with a passageway 156 defined by a chamber formed in the capillary block 142 and one wall of the support block 140. Another passageway 158 formed in the capillary block 142 couples the passageway 156 to an inlet chamber 160 which includes an increasing cross section transition section 162 at the upper end thereof and a gradually decreasing cross section transition section 164 at the lower end thereof. Thus, the fluid to be analyzed is pumped from the pump 14 through the passageways 152, 154, 156 and 158, the chamber 160 including the transition sections 162 and 164 and into the slit 144.

It has been determined that the design of the slit 144 (or capillary) as well as the design of the inlet chamber 160 and the placement of the transducers 146, 148 and 150 is critical to the operation of the rheometer. Firstly, the transducers 146, 148 and 150 must be mounted in an area of fully developed fluid flow through the slit, that is, in an area when the velocity profile of the fluid flowing through the slit (or capillary) is constant and there is no acceleration or deceleration of the fluid. Also, the transducers must be mounted along a line parallel to a straight constant velocity line (Isovel). There must be no dead space in the chamber 160 where fluid may collect. Consequently, there must be no abrupt transition in cross sectional area of the chamber 160 and the transition sections 162 and 164 are provided to avoid such an abrupt transition. However, the angles formed by the walls of the transition sections 162 and 164 must not be so narrow as to interfere with the natural stream lines of flow within the chamber nor constrict the flow of the fluid, particularly in the transition section 164. Finally, the central section of the inlet chamber 160 must be sufficiently long to allow the stream lines to reach the full diameter of the chamber (when a circular cross section chamber is used), and for the flow lines to flow parallel to each other prior to reaching the transition section 164.

As can be appreciated from the above discussion, the various requirements imposed on the inlet chamber result in an inlet chamber having a rather complex shape. Moreover, in addition to the considerations described above, the shape of the inlet chamber 160 is also affected by the parameters of the fluid being analyzed. Consequently, different inlet chambers must be provided when fluids of widely varying physical parameters are being analyzed. Therefore, in accordance with yet another important aspect of the present invention, the inlet chamber 160 is positioned with respect to the slit 144 (or capillary) in such a manner that the longitudinal axis of the chamber 160 is skewed with respect to the longitudinal axis of the slit 144 (or capillary). Such a design greatly facilitates the exchange of various inlet chambers by providing only a single contact surface 166 between the support block 140 and the capillary block 142, thereby greatly reducing sealing problems between the support block 140 and the capillary block 142. In addition, since only a single mating surface 166 is necessary, the inlet chamber 160 need not be disassembled whenever a new inlet chamber is required, but rather, the entire capillary block 142 may be removed and replaced with another capillary block by simply removing and replacing the screws fastening the capillary block 142 to the supporting block 140. Also, as a result of such a design, the transducers 146, 148 and 150, which are mounted within the support block 140, need not be disturbed when capillary blocks are interchanged.

III. Description of Operation

The three signals from the three pressure transducers 146, 148 and 150 are applied to the control console 18 for processing by the microprocessor 20 which is programmed to obtain the following information from the three pressure signals:

1. True viscosity ($\eta_{true}$) in poise,
2. First normal stress difference ($N_1$) in kilodynes per square centimeter (a measure of elasticity), and
3. True shear rate ($\dot{\gamma}_{true}$) in sec. $^{-1}$.

The above quantities are obtained by operating on the following known physical parameters of the rheometer, its operating conditions and pressure measurements which are defined as follows:

1. Q = flow rate of fluid through the rheometer in cubic centimeters per second
2. $P_1$, $P_2$, $P_3$ = the pressure in pounds per square inch measured by each of the three pressure transducers 146, 148 and 150, respectively
3. $Z_1$, $Z_2$, $Z_3$ = the positions of the respective pressure transducers 146, 148 and 150 along the slit 144 (or capillary)
4. $P_{exit}$ = calculated exit pressure in pounds per square inch
5. h = slit height in inches
6. w = slit width in inches
7. l = slit length in inches The above parameters are provided for a slit type rheometer for purposes of illustration; however, analogous parameters would be utilized if a capillary or other type of rheometer were to be employed. Criteria for analyzing fluids with different types of rheometers are presented in Han, C.D., *Trans. Soc. Rheol.*, 18, 163 (1974) and in Han, C.D., "Rheology in Polymer Processing," Academic Press, New York, 1976, both incorporated herein by reference. The units of measure selected have been selected for convenience, but any set of compatible units can be used. Also the calculations and equations described below are intended only to illustrate the principles by which the viscosity, elasticity and shear rate may be obtained. Thus, relatively simple equations that best illustrate the principles involved have been selected; however, it should be noted that other equations, many of which are better suited for manipulation by digital computers, may be used to achieve similar results.

In determining the true viscosity ($\eta_{true}$), the first normal stress difference ($N_1$) and the true shear rate ($\dot{\gamma}_{true}$) from the above parameters, the first step is to measure the pressure gradient ($P_{grad}$) at several flow rates, for example, five different flow rates, and extrapolate the five pressure gradients thus obtained to obtain the exit pressure ($P_{exit}$) at each of the five flow rates. The pressure gradient is determined for each of the five flow rates by the following equation:

$$P_{grad} = (P_1 - P_3)/(Z_1 - Z_3) \tag{1}$$

Figure 14:
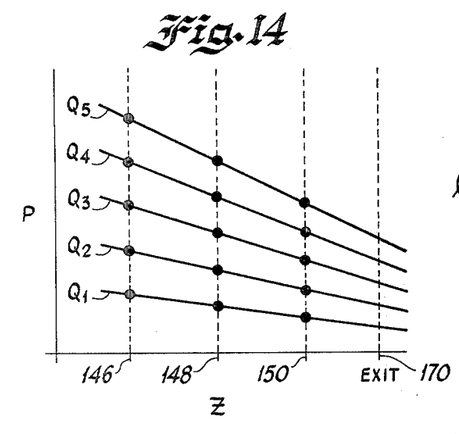
FIGS. 14–16 are plots of various measured and calculated parameters used to calculate the viscosity and elasticity of the fluid being analyzed by the rheometer.

The pressure gradient for five different flow rates $Q_1$-$Q_5$ are shown in FIG. 14 which illustrates the pressure gradient graphically. As can be seen from FIG. 14, data points are taken for each flow rate at positions corresponding to each of the transducers 146, 148 and 150, and if greater accuracy is desired, the gradient may be calculated by obtaining a best straight line fit through the three points rather than by utilizing the simple expression defined above to determine the pressure gradient. After the best fit curve has been calculated, the exit pressure ($P_{exit}$) is calculated by extrapolating each of the curves to the point where it intersects the vertical line drawn from the point on the horizontal axis representing the exit of the slit or die 170. Mathematically, the exit pressure ($P_{exit}$) may be calculated from the pressure gradient ($P_{grad}$), the length of the slit (l), the positions of the transducers ($Z_1$, $Z_2$, $Z_3$) and the measured pressure ($P_1$, $P_2$, $P_3$).

After the pressure gradient ($P_{grad}$) and exit pressure ($P_{exit}$) have been determined for each of the flow rates, the shear stress ($T_w$) at the wall of the slit is calculated for each of the flow rates from the following relation:

$$T_w = (P_{grad}) \times \frac{h}{2} \tag{2}$$

Figure 15:
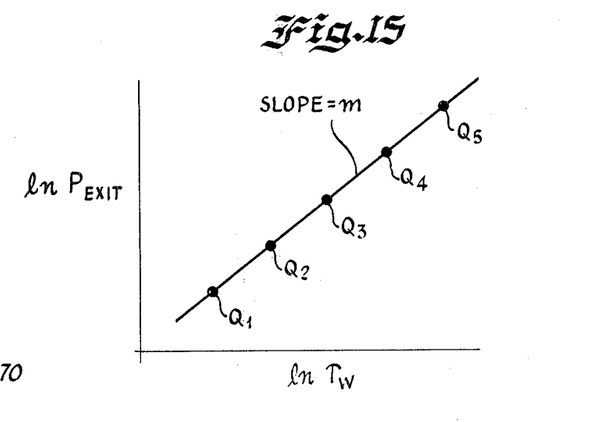

Once the exit pressure and shear stress have been calculated for each of the flow rates, the logarithm (in the present embodiment, the natural logarithm) of each of the exit pressures is plotted against the logarithm of each of the shear stresses, as indicated in FIG. 15. By using curve fitting techniques, the best straight line fit through each of the data points $Q_1$-$Q_5$ is obtained, and the slope (m) of the line is determined by determining the change in the logarithm of the exit pressure over a corresponding change in the logarithm of the shear stress as follows:

$$m = \frac{\Delta \ln P_{exit}}{\Delta \ln T_w} \tag{3}$$

Once the slope (m) has been calculated, it is a simple matter to calculate the first normal stress difference ($N_1$) which is a measure of elasticity of the fluid from the slope (m) and exit pressure ($P_{exit}$) at each flow rate as follows:

$$N_1 = P_{exit}(1+m) \tag{4}$$

The apparent shear rate ($\dot{\gamma}_{app}$) at each of the flow rates is calculated from the flow rate (Q) and the width (w) and height (h) of the slit as follows:

$$\dot{\gamma}_{app} = \frac{6Q}{wh^2} \tag{5}$$

Figure 16:
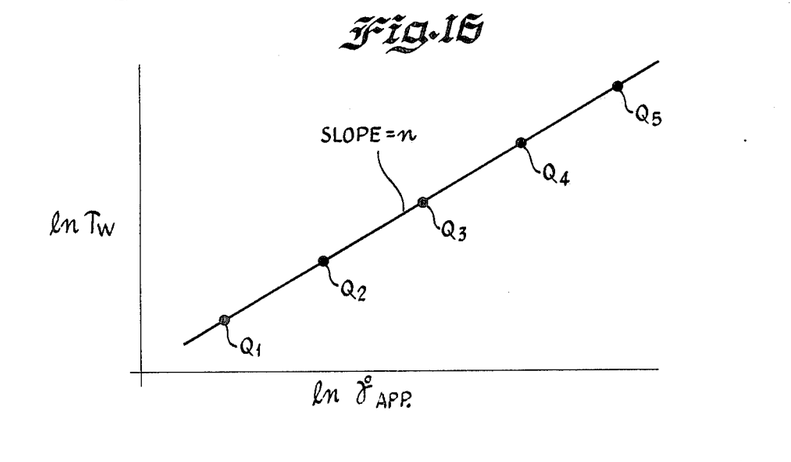

The logarithm of the apparent shear rate is then plotted against the logarithm of the shear stress (FIG. 16) for each of the flow rates and a best fit straight line is fitted to the five data points. The slope (n) of the line is calculated by comparing the difference in the logarithm of the shear stress to a corresponding difference in the logarithm of the apparent shear by the following equation:

$$n = \frac{\Delta \ln T_w}{\Delta \ln \dot{\gamma}_{app}} \tag{6}$$

The true shear rate ($\dot{\gamma}_{true}$) is calculated from the slope (n) and the apparent shear rate at each of the flow rates as follows:

$$\dot{\gamma}_{true} = \left(\frac{2n+1}{3n}\right) \dot{\gamma}_{app} \tag{7}$$

The true viscosity ($\eta_{true}$) is then readily calculated from the true shear rate ($\dot{\gamma}_{true}$) and the shear stress ($T_w$) at each of the flow rates as follows:

$$\eta_{true} = \frac{T_w}{\dot{\gamma}_{true}} \quad (8)$$

Thus, it can be seen that three important parameters can readily and continuously be calculated.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. Apparatus for measuring the viscosity and elasticity of a fluid comprising, an elongated entrance chamber having a uniform cross sectional area, an elongated restriction having a constant cross sectional area substantially smaller than the cross sectional area of said entrance chamber, and a transition section coupling said entrance chamber and said restriction, said entrance chamber being disposed with respect to said restriction such that the longitudinal axis of said entrance chamber is skewed with respect to the longitudinal axis of said restriction, and means including a plurality of pressure transducers disposed along said restriction for measuring the pressure gradient along the length of said restriction.

2. Apparatus as recited in claim 1, wherein said inlet chamber is cylindrical in shape.

3. Apparatus as recited in claim 2, wherein said restriction is cylindrical in shape.

4. Apparatus as recited in claim 3, wherein said restriction comprises a slit.

5. Apparatus as recited in claim 4, wherein said slit has a predetermined height and a predetermined width, the width of said slit being on the order of approximately 10 times greater than the height of said slit.

6. Apparatus as recited in claim 5, wherein said entrance chamber has a circular cross section.

7. A rheometer system comprising:
a die having an inlet chamber and an elongated restriction communicating with said inlet chamber;
means including a plurality of pressure transducers disposed along said restriction for providing a plurality of pressure signals representative of the pressures at a corresponding plurality of points along said restriction;
means including a metering pump coupled to said inlet chamber for applying a fluid under pressure to said inlet chamber at a predetermined flow rate;
means including an electric motor mechanically coupled to said pump for driving said pump at a predetermined speed corresponding to said predetermined flow rate;
means coupled to said driving means for providing a signal representative of the speed of said pump; and
computing means including speed controlling means coupled to said driving means and responsive to said speed signal providing means for rendering said driving means operative to drive said pump at said predetermined speed, said computing means further including means responsive to said pressure signals for providing an indication of the elasticity of said fluid.

8. A rheometer system as recited in claim 7, wherein said computing means further includes means for providing a representation of the viscosity of the fluid.

9. A rheometer system as recited in claim 7, wherein said speed controlling means includes means for automatically altering the speed of said pump from said predetermined speed to a second predetermined speed after said pump has been operated at said predetermined speed for a predetermined time duration.

10. A rheometer system as recited in claim 9, wherein said speed controlling means includes means for automatically altering the speed of said pump from said predetermined speed to said second predetermined speed at a predetermined rate.

11. A rheometer system as recited in claim 9, wherein said speed controlling means includes means for returning the speed of said pump to said predetermined speed after said pump has been operated at said second predetermined speed, said speed returning means including means for reversing the operation of said pump for a predetermined time interval prior to returning the speed of said pump to said predetermined speed.

12. A rheometer system as recited in claim 9, wherein said speed controlling means includes means for returning the speed of said pump to said predetermined speed after said pump has been operated at said second predetermined speed, said speed returning means including means for reducing the speed of said pump to a speed below said predetermined speed for a predetermined time interval prior to returning the speed of said pump to said predetermined speed.

13. A rheometer system as recited in claim 9, wherein said speed controlling means includes means for returning the speed of said pump to said predetermined speed after said pump has been operated at said second predetermined speed, said speed returning means including means for stopping said pump for a predetermined time interval prior to returning the speed of said pump to said predetermined speed.

14. A rheometer system as recited in claim 10, wherein said computing means includes data entry means for entering said predetermined speed, said second predetermined speed, said predetermined time interval and said predetermined rate.

15. A rheometer system as recited in claim 7, wherein said computing means further includes means for automatically restricting the maximum speed of said pump to a maximum speed corresponding to a predetermined maximum pressure of said fluid.

16. A rheometer system as recited in claim 7, wherein said speed representative signal providing means includes a tachometer that provides an alternating current signal having a frequency proportional to the speed of said pump, and said speed controlling means includes an alternating current signal generating means for providing an alternating current signal having a frequency proportional to said predetermined pump speed and comparing means coupled to said tachometer and said alternating current signal providing means and to said driving means for rendering said driving means operative to adjust the speed of said electric motor until the frequency of the alternating current signal provided by said tachometer is substantially equal to the frequency of the alternating current signal provided by the alternating current signal providing means.

17. A rheometer system as recited in claim 16, wherein said speed controlling means includes means for altering the frequency of the alternating current signal provided by said alternating current signal providing means to thereby alter the speed of said pump.

18. A rheometer system as recited in claim 7, wherein said transducers are disposed along said restriction in a region of fully developed flow.

19. A rheometer system as recited in claim 18, wherein said restriction is an elongated slit.

20. A rheometer system as recited in claim 7, further including heating means disposed along said inlet chamber and along said restriction for independently heating said inlet chamber and said restriction, means responsive to the temperature of said inlet chamber and said restriction, wherein said computing means includes means responsive to said temperature sensing means for controlling said heating means to thereby independently control the temperatures of said inlet chamber and said restriction.

* * * * *